Figure 1:
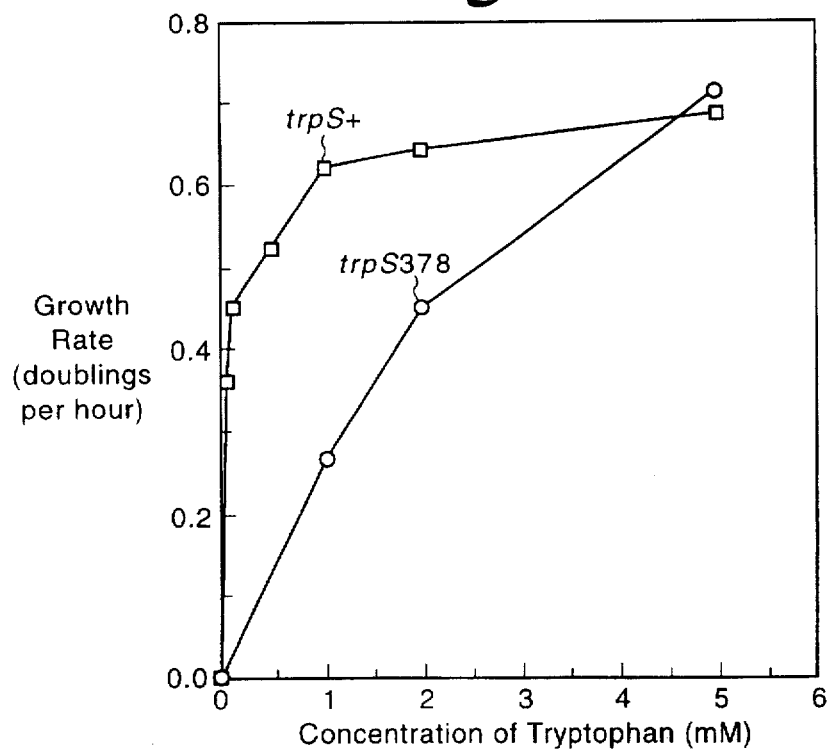

United States Patent [19]

Camakaris et al.

[11] Patent Number: 5,756,345
[45] Date of Patent: May 26, 1998

[54] **PRODUCTION OF TRYPTOPHAN BY THE BACTERIUM *ESCHERICHIA COLI***

[75] Inventors: Helen Camakaris, Eaglemont; Peter Cowan, Brighton; James Pittard, Research, all of Australia

[73] Assignee: Degussa Aktiengesellschaft, Frankfurt, Germany

[21] Appl. No.: 708,752

[22] Filed: Sep. 5, 1996

[30] Foreign Application Priority Data

Sep. 5, 1995 [GB] United Kingdom .................. 9518076

[51] Int. Cl.$^6$ .......................... C12N 1/20; C12N 15/00; C12P 21/06; C07H 21/04
[52] U.S. Cl. .................. 435/252.33; 435/69.1; 435/320.1; 435/108; 536/23.1; 536/23.2; 536/23.7
[58] Field of Search ............... 435/252.33, 320.1, 435/108, 183; 536/23.1, 23.2, 23.7

[56] References Cited

U.S. PATENT DOCUMENTS

| | | | |
|---|---|---|---|
| 4,371,614 | 2/1983 | Anderson et al. | 435/108 |
| 4,743,546 | 5/1988 | Backman et al. | 435/108 |

OTHER PUBLICATIONS

Tribe et al. Applied & Environmental Microbiol. 38(2):181, Aug., 1979.
Ito et al. J. Bacteriol. 99(1) : 279, Jul., 1969.
Brown, J. Bacteriol. 104(1) : 177, Oct., 1970.
Hiraga et al. J. Bacteriol. 96(5): 1880, Nov., 1968.
Hirahara et al Applied & Environmental Microbiology 58(8):2633, Aug., 1992.
Derwent Abstract No. 86–329946/50 and JP610247393A dated Nov. 4, 1986.
Derwent Abstract No. 87–296025/42 and JP620208284A dated Sep. 12, 1987.

*Primary Examiner*—Robert A. Wax
*Assistant Examiner*—Tekchand Saidha
*Attorney, Agent, or Firm*—Cushman Darby & Cushman IP Group of Pillsbury Madison & Sutro LLP

[57] ABSTRACT

This invention is concerned with the production of L-tryptophan by strains of *Escherichia coli*.

The invention provides a host and method for growing that host such that plasmids can be stably maintained in the absence of antibiotics, leading to high productivity of tryptophan in fermentation. It offers significant improvements over previous methods and produces tryptophan free from any contamination by tyrosine an phenylalanine thus simplifying downstream processing.

The *E. coli* strains having productivity for L-tryptophan comprise in their genome a mutant gene encoding a partially defective tryptophanyl-tRNA synthetase introducing a temperature-conditional tryptophan auxotrophy in the host and further mutations on the chromosome which disable the transport systems encoded by aroP, mtr and tnaB and being transformed with a plasmid containing a tryptophan operon encoding anthranilate synthase freed from feedback-inhibition by tryptophan.

16 Claims, 6 Drawing Sheets

PRODUCTION OF TRYPTOPHAN BY THE BACTERIUM *ESCHERICHIA COLI*

1. BACKGROUND OF THE INVENTION

This invention is concerned with the production of tryptophan by the bacterium *Escherichia coli*.

The invention provides a host and method for growing that host such that plasmids can be stably maintained in the absence of antibiotics, leading to high productivity of tryptophan in fermentation. It offers significant improvements over previous methods and produces tryptophan free from any contamination by tyrosine and phenylalanine thus simplifying downstream processing.

4. BRIEF DESCRIPTION OF THE PRIOR ART

There are now numerous examples of the genetic manipulation of microorganisms to make strains that efficiently overproduce particular amino acids.

It is generally accepted in the Art that it is necessary to interfere with normal regulatory circuits that control the expression of genes for biosynthetic pathways, to select mutants whose enzymes are no longer subject to feedback inhibition, and to disable any enzymes which break down the desired product, if any success is to be obtained with the production of particular amino acids. It has also been found useful to increase the copy numbers of certain biosynthetic genes in the cell by introducing into the cell additional gene copies on plasmids. These general principles may be found in Tribe, D. E. and J. Pittard. (1979). Appl. Environ. Microbiol. 38: 181–190, in particular as they relate to tryptophan production.

The significance of feedback inhibition of the first enzymes in the aromatic pathway (the DAHP synthases) and of the first enzyme in the terminal tryptophan pathway, and the need to abolish inhibition, is demonstrated there too Similarly, it has long been known that it is necessary to inactivate the trpR repressor protein which represses the expression of the genes of the tryptophan operon. This is discussed in the above-mentioned publication.

In the case of the tryptophan genes in *E. coli* there is a second system of control called attenuation. Even in trpR cells, tryptophan or, more specifically, charged tryptophanyl-tRNA controls expression of the tryptophan operon. When charged tryptophanyl-tRNA is present in excess, transcription of the mRNA for the trp operon genes terminates before reaching the sequences coding for the biosynthetic enzymes in about nine of every ten transcripts (Yanofsky. C. (1981)). Nature (London) 289: 751–758). This premature termination of transcription can be prevented by various genetic manipulations such as cloning the trp genes after a heterologous promoter or by deleting the attenuator locus. Tribe and Pittard (Appl. Environ. Microbiol. (1979). 38: 181–190) reported a different strategy to overcome attenuation in which they used a mutant that contained a partially defective tryptophanyl-tRNA synthetase enzyme.

When plasmids containing the structural genes for the trp operon are introduced into a cell in which the expression of these trp genes is no longer controlled and in the absence of any strong selection for the plasmid-encoded functions, subsequent multiplication of that cell and its progeny frequently results in plasmid loss from the population. If the original host is a tryptophan prototroph, cells which have lost the plasmid grow more rapidly than cells which retain it, as also do cells in which genetic events (such as deletions or insertions) have reduced or prevented expression of the trp genes present on the plasmid. Over a number of generations, such defective cells (segregants and mutants) become the predominant members of the population and if this population is the basis for a fermentation, the fermentation fails.

Various strategies have been advanced for stabilising plasmid inheritance. A method frequently used is to include a gene for antibiotic resistance on the plasmid and to add antibiotics to the fermentation broth. This method is, however, costly and may provide an environmental hazard. Strategies using a host defective in the biosynthesis of some compound required for growth, together with a plasmid carrying a gene complementing the mutant defect, have been used previously (for example in Anderson et al., U.S. Pat. No. 4,371,614), but segregants can accumulate as they continue to synthesize the nutrient for several generations (phenotypic lag). Where the requirement is the same as the nutrient being accumulated, segregants may also be fed by the nutrient which has been accumulated. A limited improvement has been achieved using hosts defective in transport, but this was achieved only under conditions where tryptophan in the medium was low (Imanaka, Patent Disclosure A No. 3-3074).

A need continues to exist for microorganisms capable of producing high levels of tryptophan. Connected is the need for a method to stabilize plasmid inheritance in said microorganisms.

3. SUMMARY OF THE INVENTION

These and other objectives of the invention which will hereinafter become more readily apparent have been attained by providing: *E. coli* K-12 strains having productivity for tryptophan and comprising in their genome a mutant gene encoding a partially defective tryptophanyl-tRNA synthetase, introducing a temperature-conditional tryptophan auxotrophy in the host and further mutations on the chromosome which disable the transport systems encoded by aroP, mtr and tnaB, such strains containing a trpE allele encoding anthranilate synthase resistant to feedback-inhibition at high concentrations of tryptophan.

Another objective of the invention has been attained by providing a method for producing L-tryptophan by fermentation which comprises culturing a bacterium as described hereinbefore under differing growth and production conditions, and recovering L-tryptophan produced from the culture medium.

4. DETAILED DESCRIPTION OF THE INVENTION

The present invention provides a process for high levels of L-tryptophan production by fermentation employing strains of *E. coli* K-12.

These strains having productivity for L-tryptophan comprise in their genome a mutant gene encoding a partially defective tryptophanyl-tRNA synthetase introducing a temperature-conditional tryptophan auxotrophy in the host and further mutations on the chromosome which disable the transport systems encoded by aroP, mtr and tnaB and being transformed with a plasmid containing a tryptophan operon encoding anthranilate synthase freed from feedback-inhibition by tryptophan.

As described in section 2, there exists a problem with strains overproducing a particular nutrient, where maintenance of stability is dependent only upon the host having a requirement for the over-produced nutrient, as segregants will continue to grow, firstly because of phenotypic lag and secondly, because they will readily be fed by the nutrient that has accumulated. Even if the host strain is defective in the active transport of the nutrient, the selection will only succeed when the nutrient concentration is relatively low. As is shown in FIG. 1, at levels of tryptophan such as 1 mM or greater, a tryptophan auxotroph unable to actively transport tryptophan nevertheless grows with a normal doubling time. This tryptophan concentration of 1 mM or about 0.2 g/l will be quickly reached when a tryptophan-producing strain is grown and hence the selection for plasmid stability will be rapidly lost under production conditions.

We have discovered that trp⁻ strains with a mutation especially such as trpS378, which partially inactivates the tryptophanyl-tRNA synthetase enzyme, require very high concentrations of tryptophan within the cell. FIG. 1 shows that, if the transport negative mutant also carries this trpS378 mutation, it requires at least 5 mM tryptophan for good growth to occur, even at 30° C. This means that until the tryptophan concentration in the medium reaches 1 g/l any segregants produced by plasmid loss will be at a growth disadvantage. This requirement for very high tryptophan concentrations before segregants compete well in growth is a significant improvement as it maintains selection for retention of the plasmid not only during growth of the inoculum, but also throughout most of the growth phase during the final fermentation. This combination of transport-negative mutations and especially trpS378 significantly enhances tryptophan yields when compared with trpS⁺ transport-negative combinations. Said mutations preferably disable the transport systems encoded by aroP, mtr and tnaB. Typical strains include but are not limited to strains containing the mutant alleles characterized by aroP579, mtr-24 and tnaA1.

Figure 2:
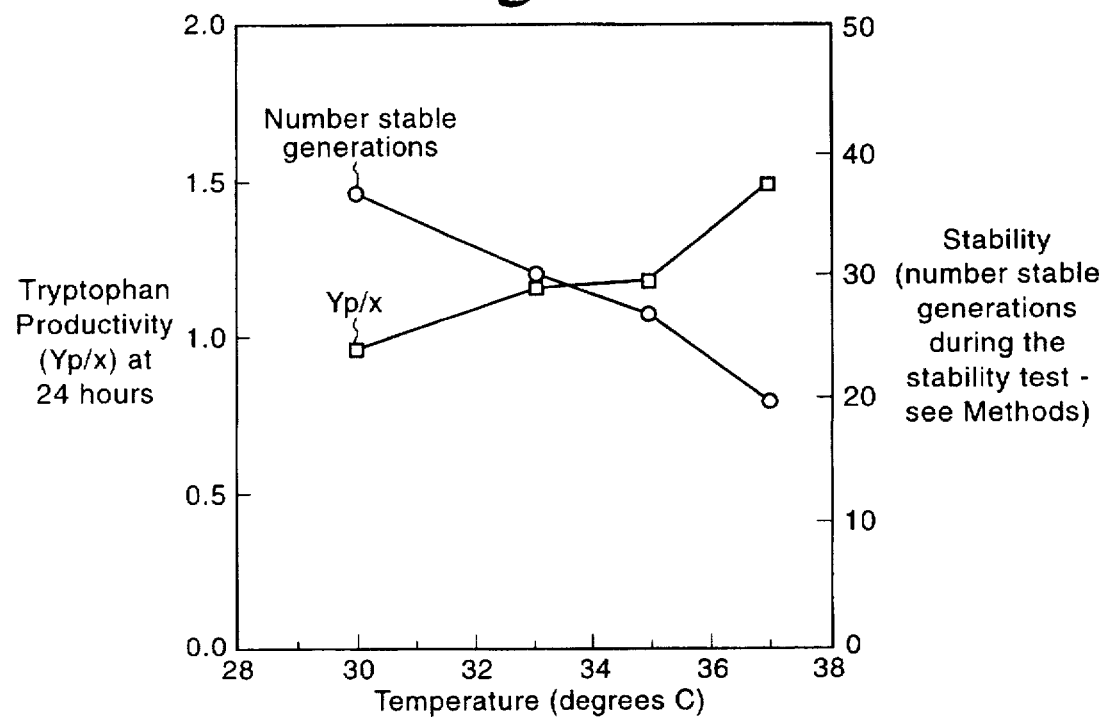

In separate experiments using an overproducing strain carrying the trpS378 allele and a plasmid carrying trpE476DCBA encoding a feedback-resistant anthranilate synthase, we have demonstrated that the temperature-sensitive allele trpS378 may be used effectively at selected temperatures to favour either stability or productivity. We have found that such production strains carrying trpS378 are more stable at about 30° C. as compared to about 37° C. At about 37° C., productivity increases and stability decreases. Results are shown in FIG. 2 for the production strain, JP6015/pMU91.

The level of stability, in this case provided by serA⁺/− complementation, can be significantly enhanced by choice of incubation temperature. Similar results are obtained for other strains.

Figure 3:
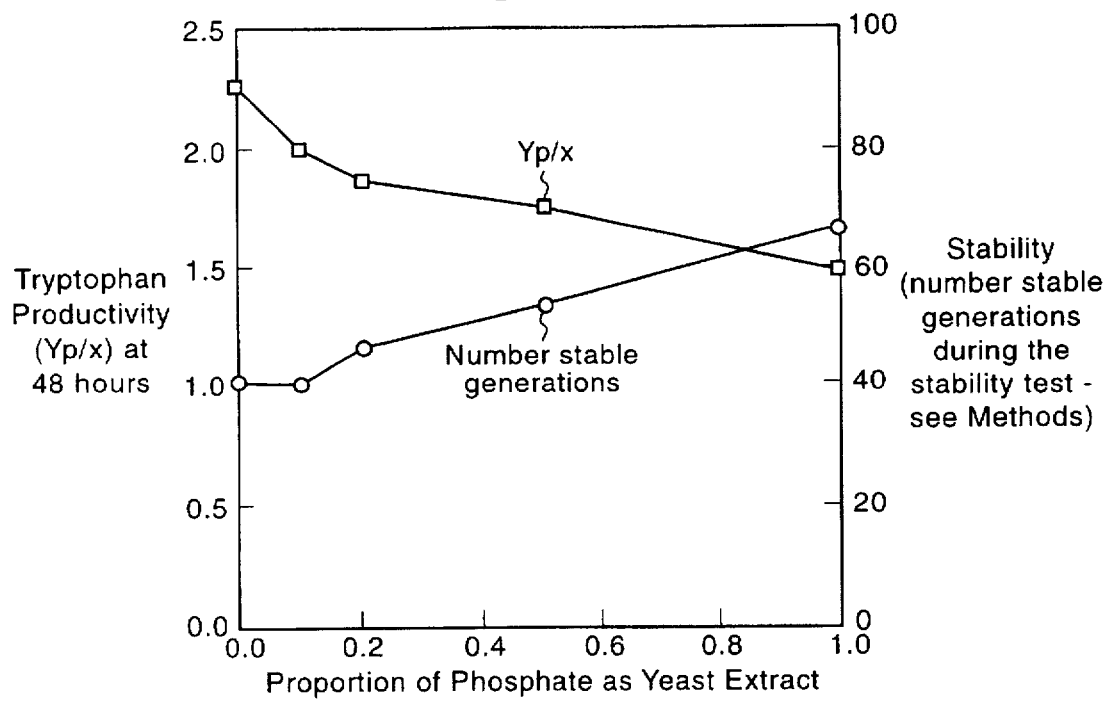

We have also established that the addition of yeast extract further decreases productivity at 30° C., such that the tryptophan level does not exceed 0.2 to 0.3 g/l. This results in a significant increase in stability as shown in FIG. 3. Some strains remain stable for more than 60 generations.

Feedback Inhibition of Anthranilate Synthase

Anthranilate synthase activity in wild-type strains of *Escherichia coli* is extremely sensitive to feedback-inhibition by tryptophan, showing about 50% inhibition at concentrations of tryptophan as low as 0.02 mM. Feedback-resistant mutants have been reported in various publications, for example, Aiba et al., Canadian Patent Application No. 1182409, Tribe and Pittard. (1979). Applied and Environmental Microbiol. 38: 1811–190, Aiba et al. (1982). Applied and Environmental Microbiol. 43: 289–297. In each case, isolation of such mutants involved selection for resistance to growth inhibition by tryptophan analogues.

Typically, mutants chosen for the purposes of tryptophan overproduction retained some feedback-inhibition, but the 50% figure occurred at a concentration of around 13 mM rather than 0.02 mM (see Aiba et al. Canadian Patent Application No. 1182409). Where mutants conferring higher feedback-resistance were described (50% inhibition values greater than 20 mM), they resulted in decreased accumulation of tryptophan, possibly because of impaired activity of the feedback-resistant enzymes (Aiba et al. (1982). Applied and Environmental Microbiol. 43: 289–297).

Two feedback-resistant mutants isolated by us were typical of those used previously in tryptophan overproduction, containing the alleles trpE476 and trpE382 encoding enzymes showing less than 10% inhibition of activity at 1 mM tryptophan (see Example 2).

When a production strain with such mutations was used in a fermenter we observed that by the end of the fermentation, for every gram of tryptophan that had accumulated there was also approximately 20–60 mg of each tyrosine and phenylalanine. Although these amino acids are a small fraction of the aromatic output they are side products which create major difficulties in the downstream recovery of tryptophan.

When we sought the basis for this accumulation we discovered that at tryptophan concentrations of 12 g/l (60 mM) these two feedback-resistant anthranilate synthases were inhibited by 60–80%. In other words, enzymes which appeared resistant at concentrations of 1 mM were unable to function effectively under the actual conditions of an industrial fermentation. No state of the art makes reference to over-producing strains with enzymes resistant to feedback-inhibition at the very high levels likely to be present in a fermentation vat, whilst maintaining normal activity, thereby improving productivity.

Figure 4:
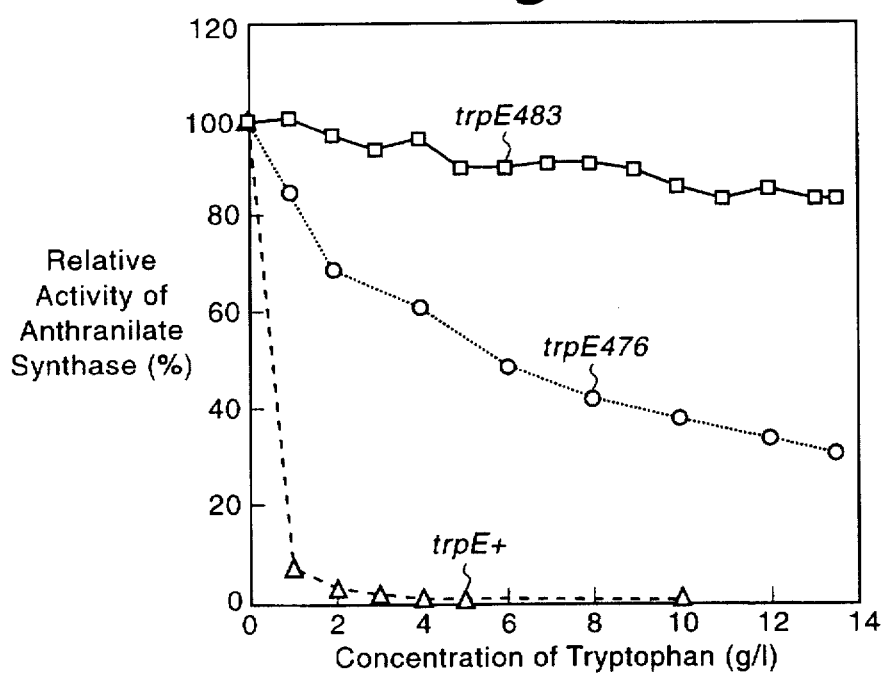

In order to overcome this problem of inhibition of anthranilate synthase at high tryptophan concentrations we isolated a new feedback-resistant mutant (trpE483) which makes an anthranilate synthase enzyme which shows less than 10% inhibition of activity at concentrations of tryptophan as high as 13.5 g/l (see FIG. 4). When production strains with the trpE483 allele were constructed and used in a fermentation under conditions which had previously produced approximately 20–60 mg of each tyrosine and phenylalanine per gram of tryptophan, no tyrosine and phenylalanine was detected and the yield of tryptophan remained high. This is in marked contrast to the earlier results reported by Aiba et al. (Applied and Environmental Microbiol. (1982) 43: 289–297) with anthranilate synthase mutants showing resistance to very high levels of tryptophan, where tryptophan productivity decreased.

The isolation of the trpE483 allele was accomplished as described in Example 2, using a plasmid carrying the trp operon. Such a plasmid carrying the trp operon may readily be constructed using the known techniques such as restriction enzyme digestion, ligation and transformation (Maniatis, T., E. F. Fritsch and J. Sambrook. Molecular Cloning: A Laboratory Manual, Cold Spring Harbor Laboratory. (1982)). The trp operon may be derived from chromosomal DNA of *E. coli* or from the specialized transducing phage, Φ80ptl90h (Hershfield, V. et al. (1974). Proc. Natl. Acad. Sci. USA. 71:3455–3459), and may be inserted into any one of a number of suitable vectors including, but not limited to, those derived from pSC101 (Cohen, S. N. and A. C. Chang (1977). J. Bacteriol: 132, 734–737), R388 (Datta, N. and R. W. Hedges (1971). J. Gen. Microbiol. 72: 349) etc. The vector may carry, in addition, the serA⁺ gene cloned by similar techniques. The plasmid so constructed is then transferred into the *E. coli* K-12 host by transformation.

The invention further relates to a method for growing and fermenting said *E. coli* K-12 strains showing high productivity. When microorganisms are grown in batch culture to produce an amino acid, the actual production of the amino acid is only required during the small number of generations which occur in the final fermentation vessel. For a 100,000 l fermenter, only 5 to 10 generations may be required in the final fermentation vessel, whereas 50 or more generations are required to provide the inoculum for that vessel.

The use of the procedures described, utilizing specific genetic mutations in conjunction with specific growth conditions, ensure the necessary strain stability whilst allowing maximum tryptophan productivity during growth in the final fermentation vessel. High yields of tryptophan may be achieved, even without the use of an antibiotic in the final fermentation (Example 6). The use of JP4735/pMU3028 results in high productivity of tryptophan with no significant formation of tyrosine and phenylalanine.

The following *E. coli* K-12 strains were deposited at the culture collection Deutsche Sammlung von Mikroorganismen und Zellkulturen (DSM) in Braunschweig (Germany) under the Budapest Treaty:

JP7847 under accession number DSM10119
JP6006 under accession number DSM10118
JP6768/pMU3018 under accession number DSM10120
JP6768/pMU3025 under accession number DSM10121
JP4735/pMU3028 under accession number DSM10122
JP6015/pMU91 under accession number DSM10123.

EXAMPLE 1

ISOLATION OF TEMPERATURE SENSITIVE TRYPTOPHAN AUXOTROPHS WITH MUTATIONS IN THE trpS GENE A strain of *Escherichia coli* K-12, KA56 (galE$^-$, thi$^-$) (Russell, R. R. B. and A. J. Pittard. (1971). J. Bacteriol. 108: 790–798) was treated with the mutagen N-methyl-N'-nitro-N-nitrosoguanidine by the method of Adelberg, Mandel and Chen (Biochem Biophys Res Commun. (1965). 18: 788–795). After treatment with mutagen, cells were washed and resuspended in minimal medium supplemented with casamino acids and with glycerol as carbon source, to utilize an enrichment procedure developed in this laboratory (Russell, R. R. B. and A. J. Pittard. (1971). J. Bacteriol. 108: 790–798). After several hours growth at 32° C., the culture was shifted to 42° C. and one hour later galactose was added to give a fmal concentration of 2%. Cells which lack uridine diphosphate galactose-4-epimerase (i.e. galE$^-$) but are able to synthesize the enzymes galactokinase and galactose-1-phosphate uridyl transferase in response to the addition of galactose, accumulate UDP galactose which is toxic to the cell and causes cell lysis (Fukasawa, T., and H. Nikaido. (1959). Nature (London). 184: 1168–1169). Cells which are unable to synthesize new enzymes in glycerol galactose casamino acids medium at 42° C. do not form this compound and are not killed. Amongst such survivors one can find temperature-sensitive auxotrophs with mutations in the trpS gene. (Casamino acids contains very low levels of tryptophan). After 5 hours at 42° C. in the presence of galactose, cells are recovered, washed and either (1) added to nutrient broth at 32° C. and cultured to mid-exponential phase or (2) spread onto nutrient agar plates to give about 200 colonies per plate and incubated for 48 hours at 32° C. The colonies on each nutrient agar plate are replicated to two plates of MM and MM supplemented with L-tryptophan at $10^{-3}$M (MM+Trp). (MM represents half-strength Medium 56 (Monod, Cohen-Bazire and Cohen. (1951).

Figure 5:
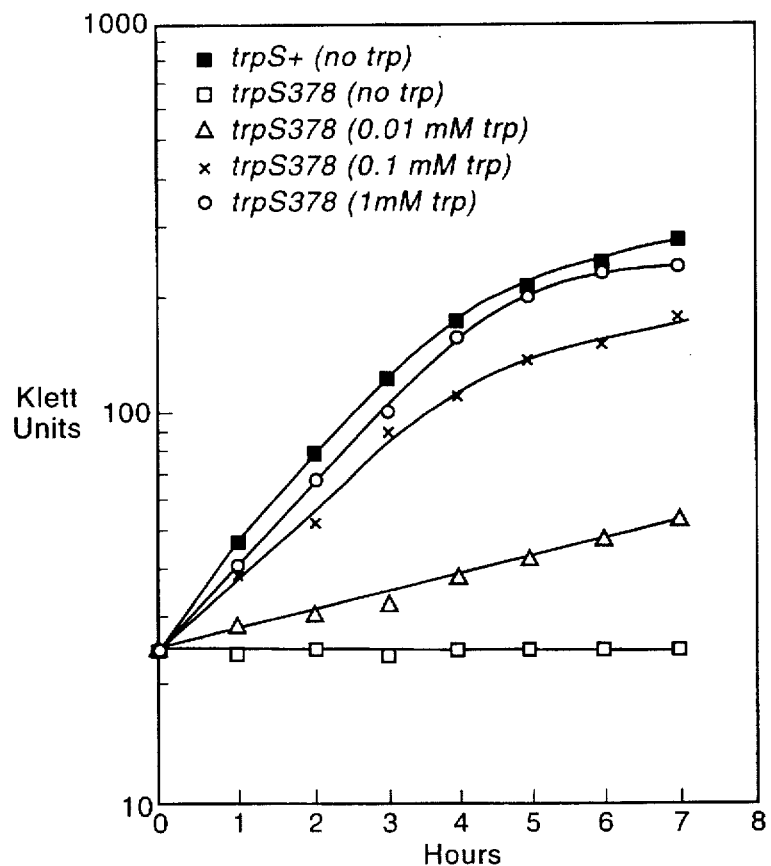

Biochim. Biophys. Acta 1, 585) solidified using 1% Oxoid No. 1 Agar, and containing glucose and thiamine. One set of plates (MM and MM+Trp), are incubated at 32° C. and the other at 42° C. Colonies which can grow on MM at 32° C. but not at 42° C. but grow on the MM+Trp medium at 42° C., are potential temperature-sensitive tryptophan auxotrophs. To identify, amongst these, mutants with alterations in the trpS gene, it is necessary to prepare P1 transducing phage on a number of clones and transduce aroB$^+$ into an aroB$^-$ mutant such as AB2826 (Pittard, J. and B. J. Wallace. (1966). J. Bacteriol. 91: 1494–1508) selecting Aro$^+$ transductants on MM at 32° C. These transductants are then tested for their ability to grow on MM and MM+Trp at 42° C. Where the original tryptophan auxotroph is mutated in the trpS gene about 50% of the Aro$^+$ transductants require tryptophan for growth at 42° C. In an alternative method the nutrient broth grown culture prepared after the galactose killing is used to prepare a P1 lysate. Again this lysate is used with AB2826 to select aroB$^+$ transductants on MM at 32° C. Such transductants are then screened for any clones which can only grow on MM at 42° C. if tryptophan is added to the medium. FIG. 5 shows the growth curves of two transductants, one being aroB$^+$ trpS378 (JP1451) and the other being aroB$^+$ trpS$^+$ (JP8820), in glucose minimal medium supplemented with various levels of tryptophan at 42° C. It can be seen that the temperature-sensitive phenotype can be reversed by high levels of tryptophan at the non-permissive temperature.

EXAMPLE 2

SELECTION OF A MUTANT OF ANTHRANILATE SYNTHASE RESISTANT TO FEEDBACK-INHIBITION BY VERY HIGH LEVELS OF TRYPTOPHAN

Figure 6A:
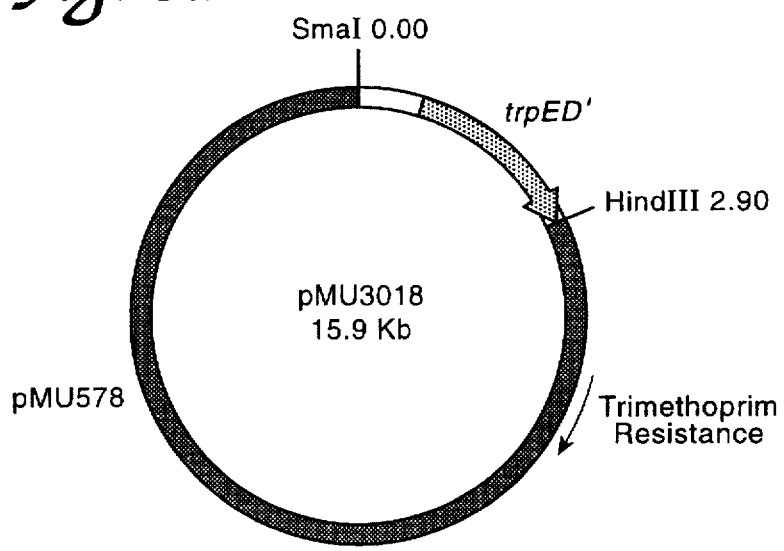
Figure 6B:
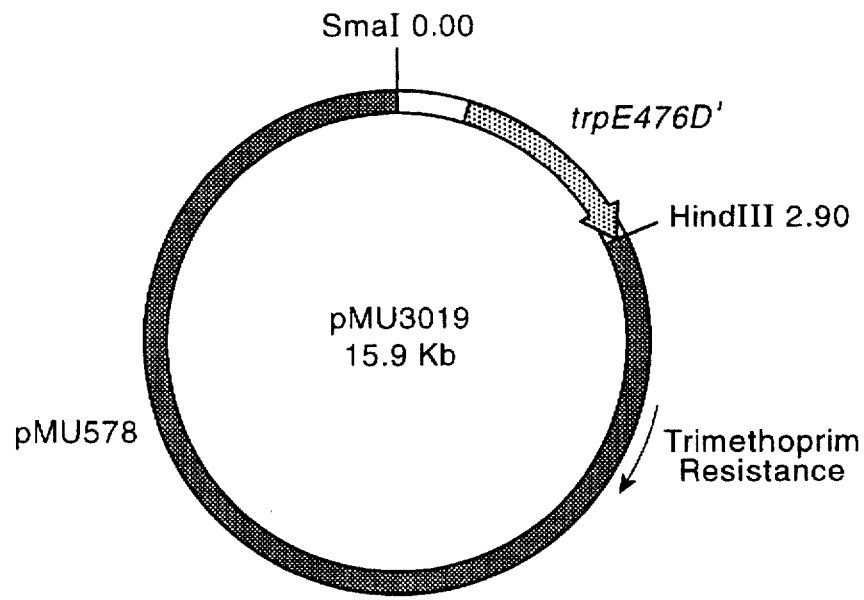

Plasmid pMU3018 (FIG. 6) carries the tip promoter, the trpE gene and part of the trpD gene on a 2.9 kb SmaI HindIII fragment. pMU3018 is derived from pMU578, which is a single-copy Tp$^R$ plasmid carrying a galK'-lac'ZA fusion, similar to the promoter cloning vector pMU575 (Andrews, A. E., B. Lawley, and A. J. Pittard. (1991). J. Bacteriol. 173: 5068–5078), but with a SmaI EcoRI BglII linker replacing the SmaI site, and the DraI fragments removed, deleting lacY and lacA. If pMU3018 DNA is digested with these two enzymes and the fragments electrophoresed in a low melting point agarose gel it is a simple matter to separate and purify the trpEtrpD' 2.9 kb fragment and the larger 13 kb vector fragment. This 2.9 kb fragment was mutagenised with 50 mM nitrous acid for 60 minutes following the method of Ray et al. (Ray, J. M., C. Yanofsky and R. Bauerle. (1988). J. Bacteriol. 170: 5500–5506), except that spermine (1 mM) was added to the mutagenesis mixture. After mutagenesis, the fragment was religated with the larger 13 kb fragment and the products of ligation were transformed into strain JP6768, an *E. coli* strain which is trpR$^-$, and in which the trpE gene has been deleted from the chromosome but trpDCB and A are fully functional (ΔtrpLE1413 (Miozzari, G. F. and C. Yanofsky. (1978). J. Bacteriol. 133: 1457–1466). Approximately 2,000 transformants were selected on Luria agar containing trimethoprim. These were screened for growth on minimal medium supplemented with the tryptophan analogue 5-fluorotryptophan at 15 mM. Clones which grew were potential feedback-resistant mutants altered in the enzyme anthranilate synthase. The anthranilate synthase activity of each of these clones was assayed in the presence of very high levels of tryptophan (13.5 g/l) using the assay described in Cho, K-O. and C. Yanofsky. (1988). J. Mol. Biol. 204: 41–50. A clone whose anthranilate synthase activity showed less than 10% inhibition at these very high levels of tryptophan was identified amongst the resistant mutants. The mutant allele present in this strain was called trpE483. In comparison, the allele trpE476 encodes an anthranilate synthase with good resistance at 1 g/l tryptophan but more than 60% inhibition at 13.5 g/l tryptophan. FIG. 4 compares the feedback sensitivity of anthranilate synthase from a strain with the wild-type allele (JP6768/pMU3018) and strains with the trpE483 allele (JP6768/pMU3025) and with the trpE476 allele (JP6768/pMU3019).

Figure 7:
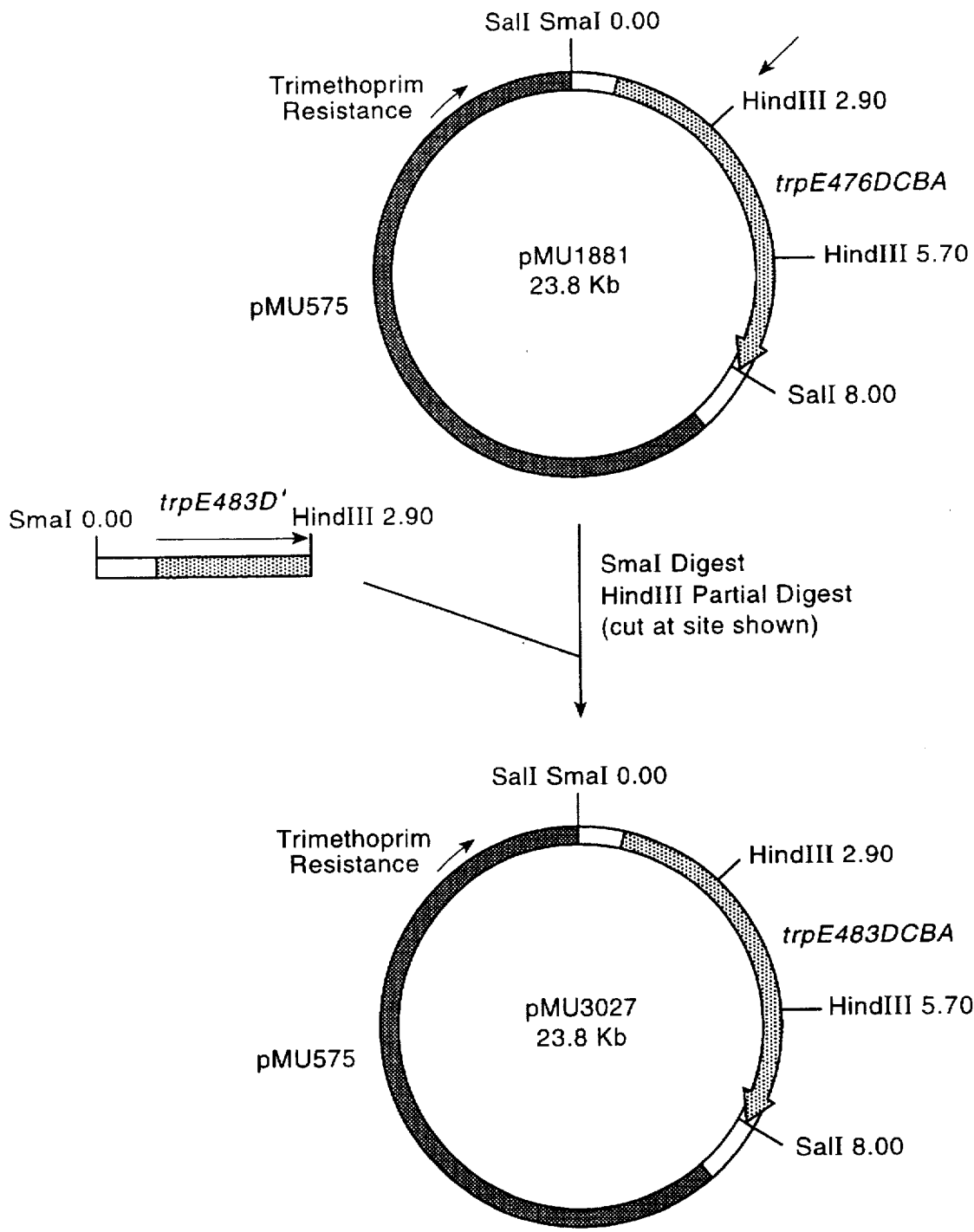
Figure 8:
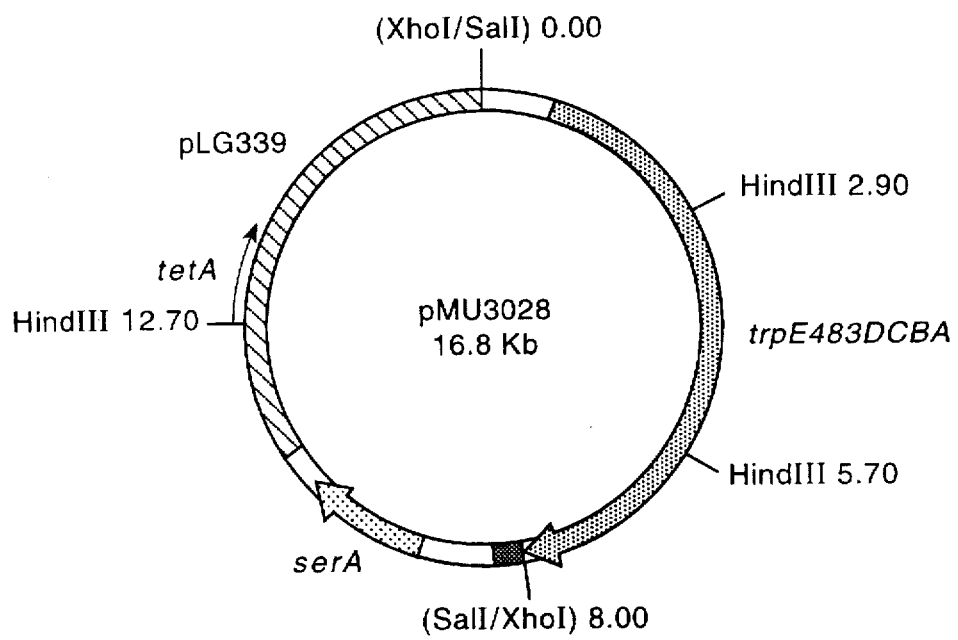

In order to reconstitute a trp operon with the trpE483 allele, the 2.9 kb fragment carrying it was joined to a 21 kb HindIII SmaI fragment from the pMU575 derivative, pMU1881, that carried the trpDCBA genes. This resulted in the plasmid pMU3027. This is summarized in FIG. 7. This new trp operon incorporating trpE483 was subsequently transferred into the pSC101-derivative pLG339 (Stoker, N. G. et al (1982), Gene 18, 335–341), carrying serA$^+$, to create pMU3028, which is shown in FIG. 8.

Under conditions in which strains with the trpE476 allele accumulated tyrosine and phenylalanine the strain with the trpE483 allele produced no detectable tyrosine at all (see Example 6). It is obvious for a person skilled in the art that a broth without side products such as tyrosine and phenylalanine is preferably used for further purification procedures.

EXAMPLE 3

CONSTRUCTION OF A STRAIN OF E. coli WITH A TEMPERATURE SENSITIVE trpS ALLELE AND MUTATIONS PREVENTING NORMAL ACTIVE TRANSPORT OF TRYPTOPHAN INTO THE CELL The genes specifying the various systems for actively transporting tryptophan into E. coli have been identified, cloned and sequenced (Sarsero, J. P., P. J. Wookey, P. Gollnick, C. Yanofsky and A. J. Pittard. (1991). J. Bacteriol. 173: 3231–3234; and Honore, N. and S. T. Cole. (1990). Nucleic Acids Research 18: 653). Mutants defective in each one of these systems (TnaB, Mtr and aroP) have also been described. The expression of the TnaB protein is prevented by a mutation in the tnaA gene (tnaA1), which has a polar effect on tnaB expression (Stewart, V. and C. Yanofsky. (1985). J. Bacteriol. 164: 731–740). This is a particularly useful mutation because the tnaA gene which is also inactivated, encodes the enzyme tryptophanase which could degrade tryptophan. Various mutations of the mtr gene have been described and mutants have been selected on the basis of resistance to the tryptophan analogue 5-methyl-tryptophan. One such mutation mtr-24 was originally described by Hiraga (Hiraga, S., K. Ito, T. Matsuyama, H. Ozeki and T. Yura. (1968). J. Bacteriol. 96: 1880–1881).

Mutants in the general aromatic transport system can also be isolated by selecting for resistance to analogues of the aromatic amino acids. The mutation aroP579 was described by Brown (Brown K. D. (1970). J. Bacteriol. 104: 177–188).

A strain which has a mutation in the trpS gene and mutations in each of the genes for the tryptophan transport systems can be constructed readily using the transposon Tn10 and Phage P1-mediated transduction. A prototrophic strain, W3110, was infected with the λTn10 transposon λNK370 and tetracycline resistant colonies were selected as described by Kleckner, N., D. F. Barker, D. G. Ross and D. Botstein. (1978). Genetics 90: 427–450. By the use of P1 transduction, isolates were obtained in which Tn10 was closely linked to aroP519, mtr-24 and tnaA1. P1 lysates could then be used to introduce each of these mutations sequentially into the trpS strain in conjunction with selection of tetracycline sensitive derivatives according to the method of Bochner, B. R., H. C. Huang, G. L. Shieven and B. N. Ames. (1980). J. Bacteriol. 143: 926–1033.

TrpS$^+$ derivatives of such mutants could be obtained by transduction with a lysate from a trpS$^+$ clone selecting for growth on plates containing 0.5 mM tryptophan at 42° C.

EXAMPLE 4

COMPARISON OF GROWTH RATES OF trpS378 AND trpS$^+$ STRAINS DEFECTIVE IN ACTIVE TRANSPORT OF TRYPTOPHAN AND IN ITS BIOSYNTHESIS Tryptophan auxotrophs that possess the wild-type trpS allele and are able to actively transport tryptophan into the cell grow at a fast rate in minimal medium supplemented with tryptophan at levels as low as $5 \times 10^{-5}$M.

Tryptophan auxotrophs defective in the active transport of tryptophan require higher levels ($\sim 10^{-3}$M) for optimal growth, whereas strains which additionally have the mutation trpS378 require concentrations as high as $5 \times 10^{-3}$M before maximum growth rate is achieved.

FIG. 1 compares the growth response to tryptophan of trpS378 and trpS$^+$ derivatives of a tryptophan auxotroph (ΔtrpLE1413) which also possesses mutations inactivating Mtr, aroP and TnaB proteins. JP6006 is derived from JP4153 by introduction of ΔtrpLE1413 by P1 transduction using TN10 as a linked marker and isolation of a tetracycline-sensitive derivative, followed by introduction of sac$^+$ by P1 transduction, using a P1 lysate grown on sac$^+$ strain GA122 (Alaeddinoglu, N. G. and H. P. Charles. (1979). J. Gen. Microbiol. 110: 47–59). JP4153 is aroF363 aroG103(FBR) aroH371(FBR) trpE382(FBR) trpR363 tyrR366 trpS378 aroP579 mtr-24 tna-1. JP7847 is a trpS$^+$ derivative of JP6006, isolated by P1 transduction.

Cells were grown in minimal medium supplemented with different levels of tryptophan at 30° C. Growth was measured by optical density with a Klett colorimeter and doubling times were calculated from the exponential phase of each growth curve.

EXAMPLE 5

THE EFFECT OF TEMPERATURE AND YEAST EXTRACT ADDITION ON STRAIN STABILITY AND PRODUCTIVITY

Strain stability may be tested by measurement of the productivity of tryptophan and anthranilate of cultures in shake flasks, where 1% serial transfers are made every 24 hours. Biomass is limited to approximately 0.4 mg/ml by phosphate concentration, by the phosphate available in yeast extract, or by a mixture of the two. Passage through each flask in the series represents a 100-fold increase in cell number, or 6.7 generations.

Tryptophan productivity characteristically remains close to 100% of the normal value for the strain, with negligible anthranilate detected, for a number of flasks. In a flask some distance down the series, tryptophan productivity generally falls suddenly to 40%–50%, with the concomitant appearance of anthranilate. Cell counts have indicated that the transition from high tryptophan productivity with no anthranilate to low tryptophan productivity with anthranilate corresponds to an increase in segregants or mutants from 0–10% to 40–70%.

The medium for each strain is prepared from sterile stock solutions as follows:

| | |
|---|---|
| glucose (20%) or sucrose (20%) | 10 ml |
| MOPS Minimal Medium (×10)* | 20 ml |
| B1 (thiamine) (0.01%) | 0.2 ml |
| phosphate (15 mM $KH_2PO_4$) | 2.0 ml |
| tetracycline (10 mg/ml), if required | 0.2 ml |
| sterile distilled water | 170 ml |

*MOPS Minimal Medium (×10) contains per liter: 167.44 g MOPS, 1.41 g $Na_3$ citrate. $2H_2O$, 0.13 g $FeSO4.7H_2O$, 19.2 g $NH_4Cl$, 4.0 g $MgSO_4.7H_2O$, 2.4 g KCl, 0.15 mg $CaCl_2.2H_2O$ and trace elements (14 µg $CoCl_2.6H_2O$, 5 µg $CuSO_4.5H_2O$, 48 µg $H_3BO_3$, 57 µg $ZnSO_4.7H_2O$, 32 µg $MnCl_2.4H_2O$ and 8 µg $(NH_4)_6Mo_7O_{24}.4H_2O$).

A 10 ml culture is inoculated from a fresh patch of the test strain, and incubated overnight with shaking at 30° C. The procedure from transformation until this stage represents about 34 generations, which are not included in the calculations. The overnight culture is used to inoculate the first flask in the series.

1% transfers (100 µl into 10 ml) are made at 24 hour intervals until the culture's productivity of tryptophan falls, with the simultaneous appearance of anthranilic acid. Under the conditions of these experiments each culture reached stationary phase before being transferred and each flask represents approximately 6.7 generations. Where the dramatic changes in tryptophan and anthranilic acid levels occurred in the sixth flask for example, stability would be recorded as 5×6.7 or 33.5 generations. At the time of each transfer the optical density of the 24 hr culture is measured, a sample is centrifuged and the supernatant is filtered through a disposable filter Millipore, 0.45 µm) using a syringe. The concentration of tryptophan and anthranilic acid are determined by HPLC.

Measurement of Productivity (Y p/x) in Flasks

The test strain is grown at the required temperature with shaking, and productivity is measured after 24 hrs and 48 hrs. The medium is the same as that used in stability trials. A 10 ml culture is inoculated from a fresh patch, and incubated overnight with shaking. This is used to inoculate the test flask, containing 15 ml of the same medium. After 24 hrs a sample is removed. Optical density is measured at 660λ using a Spectrophotometer and dry weight is calculated using a standard curve.

The sample is centrifuged, filtered, and tryptophan, tyrosine and anthranilic acid concentrations are measured by HPLC using appropriate standards. The productivity (Y p/x) is defined as yield of tryptophan (g/l) divided by yield of biomass or dry weight (g/l).

The effect of temperature of incubation on both stability and productivity for an overproducing strain carrying the trpS378 allele and a plasmid carrying the trp operon encoding a feedback-resistant anthranilate synthase, is shown in FIG. 2. Low temperatures favour high stability and low productivity, whilst higher temperatures favour productivity at the expense of stability. This may be demonstrated in various production strains, with different primary selections. The data in FIG. 2 is for JP6015/pMU91 and the primary selection is for Ser$^+$. JP6015 is derived from JP4153 (see Example 4) by introduction of sac$^+$ by transduction, and introduction of serA$^-$ by cotransduction with a closely linked Tn10 transposon, and subsequent selection of a tetracycline sensitive derivative. pMU91 is a plasmid derived from pSC101 (Cohen, S. N. and A. C. Chang (1977). J. Bacteriol. 132: 734–737), carrying Tc$^R$, trpE476DCBA and serA$^+$ (see FIG. 9). The trpE476DCBA alelle was isolated using the specialized transducing phage Φ80pt190h (Herschfield, V. et al (1974). Proc. Natl. Acad. Sci. USA 71:3455–3459). A trpE$^-$ strain carrying Φ80pt190h was plated on minimal medium containing 1 mM 5-methyltryptophan (5MT). A pool of cells was induced by ultraviolet light to produce a lysate which was used in a subsequent transduction, selecting Trp$^+$5MTR transductants. Several of these were assayed for anthranilate synthase activity, and the trpE476DCBA allele was characterized as encoding an anthranilate synthase with 70% of full activity at 10 mM L-tryptophan. The trp genes were cloned on a 7.9 kb XhoIISalI fragment into the XhoI site of pSC101. The serA$^+$ gene was introduced into the XhoI site on a 2.9 kb SalI fragment.

The effect of the presence or absence of yeast extract on both stability and productivity can also be demonstrated in various tryptophan over-producing strains The data in FIG. 3, using JP6015/pMU91 and a Ser$^+$ primary selection, demonstrates the use of yeast extract to decrease productivity and increase stability.

EXAMPLE 6

TRYPTOPHAN PRODUCTION WITH ESCHERICHIA COLI JP6015/pMU91

Single colonies of Escherichia coli K-12 strain JP6015/pMU91 were produced on MM agar (see example 1) supplemented with glucose (2 g/l), yeast extract (5 g/l) and tetracycline (5 mg/l) by incubation at 30° C. for 48 hours. One single colony was further propagated in a 10 ml culture (100 ml flask) by incubation for approximately 16 hours at 30° C. and at 250 rpm (revolution per minute).

The medium for the culture was prepared from sterile stock solutions as follows:

| | | |
|---|---|---|
| glucose (20%) | 10 ml | |
| MOPS minimal medium (×10) | 20 ml | (see Example 5) |
| yeast extract (20%) | 1 ml | |
| tetracycline (10 mg/l) | 0.1 ml | |
| sterile distilled water | 170 ml | |

Oneml of this culture of Escherichia coli K-12 strain JP6015/pMU91 was inoculated into 300 ml of a seed medium (composition shown in Table 1) charged in an Erlenmeyer's flask of 2000 ml volume, and cultured with shaking at 30° C. for 24 hours on a rotary shaker at 150 rpm.

70 ml of the resulting seed culture was inoculated into 700 ml of a pre fermentation medium (composition shown in Table 2) charged in a 2 l jar fermenter, and culturing was carried out at 30° C. for 24 hours. The pH value of 6.7 was controlled by 25% aqueous ammonia; pO$_2$ was kept above 40% by aeration with a rate of ⅓ vvm and stirring with a speed between 280 and 380 rpm.

The resulting preculture having an OD value of 20 (measured at 660 nm) was inoculated into 6.3 l of the main fermentation medium with the composition shown in Table 3, charged in a 10 l fermenter.

The fermentation was carried out at 33° C. with aeration at 0.5 vvm and keeping pO$_2$ above 40% by stirring the culture between 700 and 1200 rpm; pH was maintained at 7.0 using 25% aqueous ammonia. After 6.5 hours a solution of 620 g/l (w/v) glucose was continuously added to the culture in such a manner that the concentration of glucose in the fermenter did not exceed the value of 17 g/l. After 32 hours the fermentation was completed. The amount of L-tryptophan and of the side products L-phenylalanine and L-tyrosine accumulated was quantitatively determined by high performance liquid chromatography. The results are reported in Table 4.

EXAMPLE 7

TRYPTOPHAN PRODUCTION WITH ESCHERICHIA COLI JP4735/pMU3028

Single colonies of Escherichia coli K-12 strain JP4735/pMU3028 were produced on MM agar (see example 1) supplemented with glucose (2 g/l), yeast extract (5 g/l) and tetracycline (2.5 mg/l) by incubation at 30° C. for 48 hours. One single colony was further propagated in a 10 ml culture (100 ml flask) by incubation for approximately 16 hours at 30° C. and at 250 rpm (revolution per minute).

The medium of the culture was prepared from sterile stock solutions as follows:

| | | |
|---|---|---|
| glucose (20%) | 10 ml | |
| MOPS minimal medium (×10) | 20 ml | (see Example 5) |
| yeast extract (20%) | 1 ml | |
| tetracycline (10 mg/l) | 0.05 ml | |
| sterile distilled water | 170 ml | |

One ml of this culture of Escherichia coli K-12 strain JP4735/pMU3028 was inoculated into 300 ml of a seed medium (composition shown in Table 1) charged in an Erlenmeyer's flask of 2000 ml volume, and cultured with shaking at 30° C. for 24 hours on a rotary shaker at 150 rpm. 70 ml of the resulting seed culture was inoculated into 700 ml of a pre fermentation medium (composition shown in Table 2) charged in a 2 l jar fermenter, and culturing was carried out at 30° C. for 24 hours. The pH value of 6.7 was controlled by 25% aqueous ammonia; $pO_2$ was kept above 40% by aeration with a rate of ⅓ vvm and stirring with a speed between 280 and 380 rpm.

The resulting preculture having an OD value of 20 (measured at 660 nm) was inoculated into 6.3 l of the fermentation medium with the composition shown in Table 3, charged in a 10 l fermenter.

The fermentation was carried out at 33° C. with aeration at 0.5 vvm and keeping $pO_2$ above 40% by stirring the culture between 700 and 1200 rpm; pH was maintained at 7.0 using 25% aqueous ammonia. After 6.5 hours a solution of 620 g/l (w/v) glucose was continuously added to the culture in such a manner that the concentration of glucose in the fermenter did not exceed the value of 27 g/l. After 45 hours the fermentation was completed. The amount of L-tryptophan accumulated was quantitatively determined by high performance liquid chromatography. The results are reported in Table 4.

TABLE 1

| Composition of Seed Medium | |
|---|---|
| glucose*$H_2O$ | 4 g/l |
| yeast extract | 1.1 g/l |
| morpholino-propane sulfonic acid | 16.7 g/l |
| tri sodium citrate*$2H_2O$ | 0.14 g/l |
| $FeSO_4$*$7H_2O$ | 13 mg/l |
| $MgSO_4$*$7H_2O$ | 0.4 g/l |
| $(NH_4)_2SO_4$ | 1.29 g/l |
| KCl | 0.24 g/l |
| $KH_2PO_4$ | 1.05 g/l |
| thiamine hydrochloride | 5 mg/l |
| tetracycline | 2.5 mg/l |
| trace elements | 2 ml/l | pH adjustment to approx. 7.0 with 25% aqueous $NH_4OH$

The trace elements are comprising:

| | |
|---|---|
| $Na_2MoO_4$*$H_2O$ | 0.15 g/l |
| $H_3BO_3$ | 2.5 g/l |
| $CoCl_2$*$6H_2O$ | 0.7 g/l |
| $CuSO_4$*$5H_2O$ | 0.25 g/l |
| $MnCl_2$*$4H_2O$ | 1.6 g/l |
| $ZnSO_4$*$7H_2O$ | 0.3 g/l |

TABLE 2

| Composition of Pre Fermentation Medium | |
|---|---|
| glucose*$H_2O$ | 27.5 g/l |
| yeast extract | 7.5 g/l |
| tri sodium citrate*$2H_2O$ | 1 g/l |
| $FeSO_4$*$7H_2O$ | 1.1 g/l |
| $MgSO_4$*$7H_2O$ | 3.15 g/l |
| $(NH_4)_2SO_4$ | 8.65 g/l |
| $KH_2PO_4$ | 0.75 g/l |
| thiamine hydrochloride | 24 mg/l |
| tetracycline | 2.5 mg/l |
| $K_2SO_4$ | 2.3 g/l |
| trace elements (see table 1) | 2 ml/l |

TABLE 3

| Composition of Main Fermentation Medium | |
|---|---|
| glucose*$H_2O$ | 27.5 g/l |
| tri sodium citrate*$2H_2O$ | 1 g/l |
| $FeSO_4$*$7H_2O$ | 1.4 g/l |
| $MgSO_4$*$7H_2O$ | 3.15 g/l |
| $(NH_4)_2SO_4$ | 8.65 g/l |
| $KH_2PO_4$ | 1.5 g/l |
| $K_2SO_4$ | 2.3 g/l |
| trace elements (see table 1) | 4 ml/l |

TABLE 4

| Strain | L-Tryptophan (g/l) | L-Phenylalanine (g/l) | L-Tyrosine (g/l) |
|---|---|---|---|
| JP6015/pMU91 | 18.3 | 1.0 | 0.8 |
| JP4735/pMU3028 | 19.5 | 0 | 0 |

We claim:

1. An E. coli strain having increased productivity for L-tryptophan, said strain comprising a genome having a mutant trpS gene encoding a defective tryptophanyl-tRNA synthetase, said synthetase being characterized by a temperature-dependent tryptophan auxotrophy and selected at 27°–30° C., and said strain having a further mutation in at least one gene selected from the group consisting of mtr, aroP, tnaA and tnaB, thereby rendering the strain defective in tryptophan transport.

2. The strain according to claim 1, wherein said further mutation is selected from the group consisting of aroP579, mtr-24 and tnaA1.

3. The strain according to claim 1 or 2, wherein said mutant gene encoding defective tryptophanyl-tRNA synthetase is the trpS378 allele, present in *E. coli* JP6006 deposited with DSM (Deutsche Sammlung fur Mikroorganismen, Braunschweig, Germany) under accession number DSM10118.

4. The strain according to claim 1 or 2, said strain carrying a plasmid carrying the tryptophan operon encoding an anthranilate synthase enzyme freed from feedback inhibition by tryptophan.

Figure 6C:
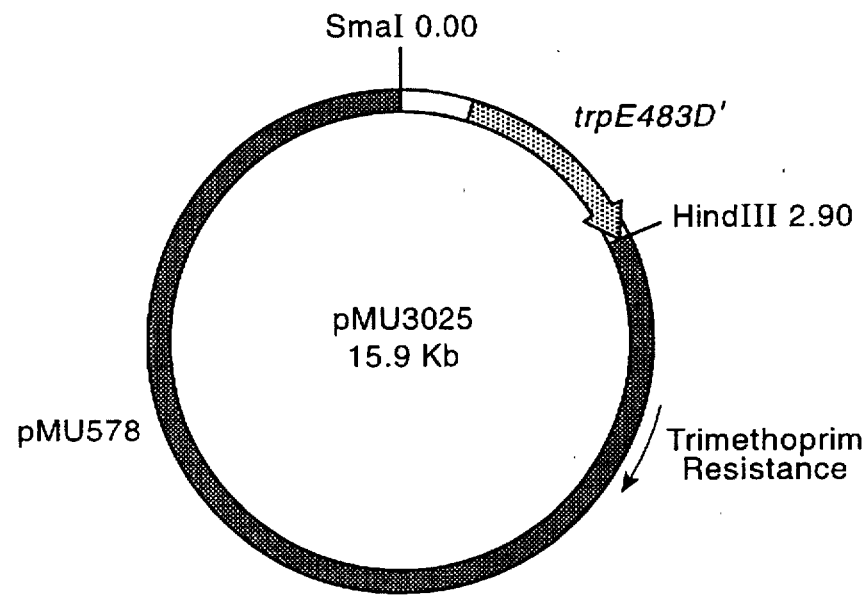

5. The strain according to claim 4, wherein said plasmid is pMU3025 and carries the trpE483 allele, said plasmid being characterized as shown in FIG. 6c and present in *E. coli* JP6768/pMU3025 deposited with DSM under the accession number DSM10121.

6. The strain according to claim 4, wherein said plasmid is pMU3028 and carries the trpE483 allele and serA$^+$, said plasmid being characterized as shown in FIG. 8 and present in *E. coli* JP4735/pMU3028, deposited with DSM under the accession number DSM10122.

Figure 9:
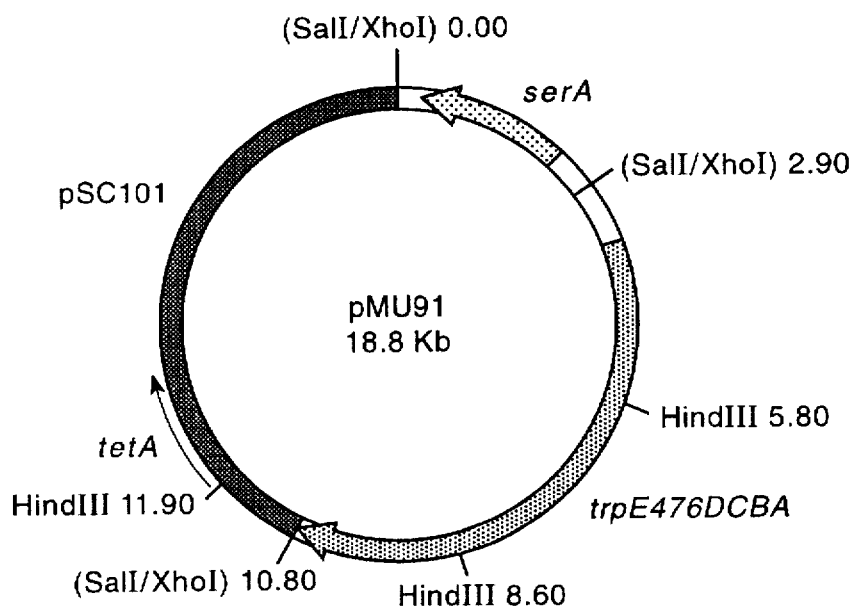

7. The strain according to claim 4, wherein said plasmid is pMU91 and carries the trpE476 DCBA genes and serA$^+$, said plasmid being characterized as shown in FIG. 9 and obtainable from *E. coli* JP6015/pMU91, deposited with DSM under the accession number DSM10123.

8. The strain according to claim 1 or 2, said strain having at least one mutation selected from the group consisting of trpR, tyrR, serA, aroG, aroH, and trpE.

9. A method for stabilizing the characteristics of an *E. coli* strain having productivity for L-tryptophan during the growth of inoculum, said method comprising the steps of introducing into the genome of said *E. coli* strain a mutant gene encoding a partially defective tryptophanyl-tRNA synthetase, said synthetase being characterized by a temperature dependent tryptophan auxotrophy and selected at 27°–30° C.;

introducing at least one further mutation in the genes aroP, mtr, tnaA or tnaB; and cultivating said strain at 27°–30° C.

10. The method according to claim 9 wherein said mutation is selected from the group consisting of aroP579, mtr-24 and tnaA1.

11. The method according to claim 9 or 10, wherein said *E. coli* strain carries a plasmid.

12. The method according to claim 11, wherein said plasmid carries the trpE483 allele.

13. The method according to claim 9 or 10, wherein yeast extract is added during inoculum growth.

14. A method of producing L-tryptophan by fermentation which comprises:

cultivating an *E. coli* strain according to claim 1 or 2 in an appropriate culture medium at about 30° C., limiting growth by adjusting the concentration of available phosphate;

fermenting said medium at a temperature in the range of about 33° C. to 37° C., in the absence of yeast extract; and recovering tryptophan accumulated in the culture medium.

15. The method according to claim 14, wherein said cultivation is carried out in the presence of yeast extract.

16. The method according to claim 14, wherein said fermentation is carried out in the absence of antibiotics.

* * * * *